United States Patent [19]
Martinez et al.

[11] Patent Number: 5,879,335
[45] Date of Patent: Mar. 9, 1999

[54] DEVICE FOR SECURING A GENERALLY CYLINDRICAL MEMBER TO A BODY PART OR OTHER OBJECT

[76] Inventors: Darryl J. Martinez, 416 Camellia Dr.; David M. Marse, 415 Camellia Dr., both of Thibodaux, La. 70301

[21] Appl. No.: 813,254

[22] Filed: Mar. 7, 1997

[51] Int. Cl.⁶ .................................................. A61M 25/02
[52] U.S. Cl. ............................................................ 604/179
[58] Field of Search ................................. 609/174, 179, 609/180; 128/DIG. 26

[56] References Cited

U.S. PATENT DOCUMENTS

| | | | |
|---|---|---|---|
| 3,726,280 | 4/1973 | Lacount | 604/179 |
| 4,088,136 | 5/1978 | Hasslinger et al. | 128/349 R |
| 4,096,863 | 6/1978 | Kaplan et al. | 128/349 R |
| 4,165,748 | 8/1979 | Johnson | 128/348 |
| 4,445,894 | 5/1984 | Kovacs | 604/179 |
| 4,569,348 | 2/1986 | Hasslinger | 604/179 |
| 4,571,245 | 2/1986 | Hubbard et al. | 604/179 |
| 4,617,017 | 10/1986 | Hubbard et al. | 604/179 |
| 4,639,980 | 2/1987 | Peterson | 128/DIG. 26 X |
| 4,665,566 | 5/1987 | Garrow | 128/DIG. 26 X |
| 4,671,787 | 6/1987 | Widman | 604/179 |
| 4,700,432 | 10/1987 | Fennell | 604/179 X |
| 4,739,757 | 4/1988 | Edwards | 128/DIG. 26 X |
| 5,167,630 | 12/1992 | Paul | 604/179 |
| 5,352,209 | 10/1994 | Bird et al. | 604/179 |

*Primary Examiner*—Max Hindenburg
*Attorney, Agent, or Firm*—John F. Sieberth; R. Andrew Patty, II

[57] ABSTRACT

A device for detachably securing a generally cylindrical member, e.g., a catheter tube, to a body part or other object, the device being easy to use and manufacture, and is disposable. The device comprises: (a) a primary strap, (b) a secondary strap comprising a connecting end portion and a free end portion, (c) fastening means for adjustably fastening the primary strap around the body part or other object, and (d) connecting means for connecting the connecting end portion to the primary strap, the secondary strap further comprising an adhesive backing which (1) extends over at least a portion of one side of the secondary strap, and (2) when a portion thereof is placed in contact with the member, holds the member in place relative to the secondary strap.

21 Claims, 7 Drawing Sheets

DEVICE FOR SECURING A GENERALLY CYLINDRICAL MEMBER TO A BODY PART OR OTHER OBJECT

TECHNICAL FIELD

This invention relates to devices which secure a generally cylindrical member, such as a tube or wire, to a body part or other object to prevent unintentional removal of an accompanying device attached to a patient and connected to the generally cylindrical member.

BACKGROUND

Emergency medical situations often call for swift action on the part of physicians, emergency medical technicians, nurses and other medical personnel. These situations call upon the use of devices, such as catheters and accompanying tubes, which carry necessary drugs and/or fluids into the body of the patient, as well as the transportation of the patient to a hospital, or from one place to another within a hospital. In the rush to apply the necessary medical treatment in such circumstances, tubes and/or wires which are connected to accompanying catheters or other devices become vulnerable to accidental pulls or snags when caught by equipment or personnel who are trying to provide medical treatment under less than ideal circumstances. Even slight displacement of these tubes or wires can disturb the site of catheter insertion or device attachment, resulting in lost time and treatment delay while medical personnel replace the particular device.

Previous attempts to address this problem have involved complicated and expensive straps employing buckles, threaded loops, and stitching to provide strap-type anchors for holding a catheter tube in place. Difficulty in use and manufacture can make such devices cumbersome and expensive to use, resulting in precious time and money wasted. In addition, some previous devices placed undue reliance upon tape to secure the device to the body part, as wet skin or other adverse conditions often prevented such tape from functioning properly. Moreover, previous devices often failed to address the costs associated with their disposal, in light of the potential exposure of the device to blood or other bodily fluids during use. A need therefore exists for a device which is easy to use, inexpensive to make, easily disposed of, and effective to secure a catheter tube to a body part or other object and to prevent unintentional displacement of an accompanying catheter. This invention is deemed to satisfy this need in a highly efficient manner.

SUMMARY OF THE INVENTION

This invention provides, among other things, a device for detachably securing a generally cylindrical member to a body part or other object. The device comprises (a) a primary strap, (b) a secondary strap comprising a connecting end portion and a free end portion, (c) fastening means for adjustably fastening the primary strap around the body part or other object, and (d) connecting means for connecting the connecting end portion to the primary strap, the secondary strap further comprising an adhesive backing which (1) extends over at least a portion of one side of the secondary strap, and (2) when a portion thereof is placed in contact with the member, holds the member in place relative to the secondary strap.

In another embodiment of this invention, a device is provided for detachably securing a generally cylindrical member to a body part or other object, the device comprising (a) a primary strap which comprises a plurality of Velcro-type female loops extending from at least a portion of one side of the primary strap, (b) a secondary strap which comprises a plurality of Velcro-type male hooks extending from at least a portion of one side of the secondary strap, and an adhesive backing extending over at least a portion of the other side of the secondary strap, one end portion of the secondary strap being connected to one end portion of the primary strap by contact between a first portion of the adhesive backing and a portion of the plurality of Velcro-type female loops. In this embodiment, the free end of the secondary strap is of sufficient length to be wrapped around at least a major portion of the circumference of the member thereby placing a second portion of the adhesive backing in contact with the member. The free end of the primary strap also is of sufficient length (1) to be wrapped around the body part or other object, and (2) to place a portion of the plurality of Velcro-type female loops in mating contact with a portion of the plurality of Velcro-type male hooks extending from the secondary strap.

This invention also provides a method of detachably securing a generally cylindrical member to a body part or other object. The method comprises (a) wrapping around the member one end of a secondary strap, the secondary strap being comprised of a plurality of Velcro-type male hooks extending from at least a portion of one side and an adhesive backing covering at least a portion of the other side, so that a first portion of the adhesive backing is in adhering contact with the member along at least a major portion of the circumference thereof, (b) wrapping around the body part or other object a primary strap, the primary strap being comprised of a plurality of Velcro-type female loops extending from at least a portion of one side, a first portion of the plurality of Velcro-type female loops being in adhering contact with another portion of the adhesive backing of the secondary strap, and (c) placing a second portion of the plurality of Velcro-type female loops of the primary strap in mating contact with a portion of the plurality of Velcro-type male hooks of the secondary strap.

These and other embodiments and features of the invention will become still further apparent from the ensuing description, appended claims and accompanying drawings.

BRIEF DESCRIPTION OF THE DRAWINGS

In the figures, like numbers are used to refer to like parts among the several figures.

DETAILED DESCRIPTION OF THE INVENTION

Figure 1:
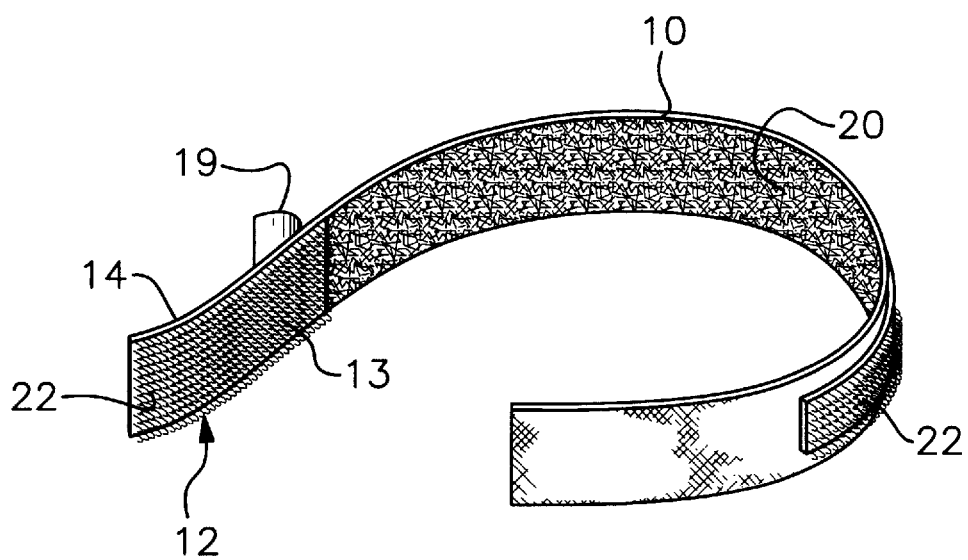
FIG. 1 is a perspective view of a preferred device of this invention.
Figure 2:
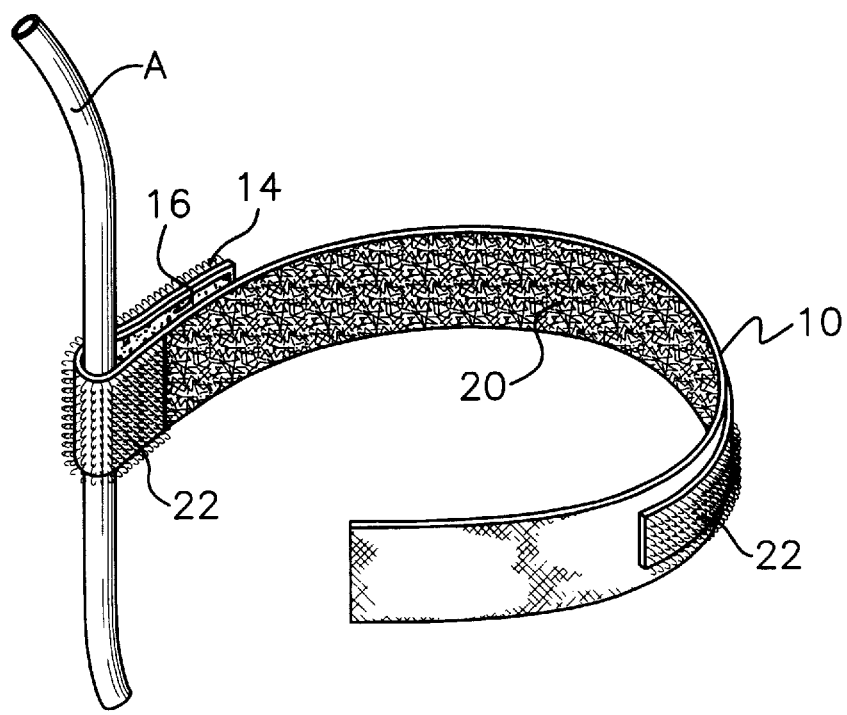
FIG. 2 is another perspective view of the device of FIG. 1 partially wrapped around a catheter tube, the tube being partially broken away.
Figure 3:
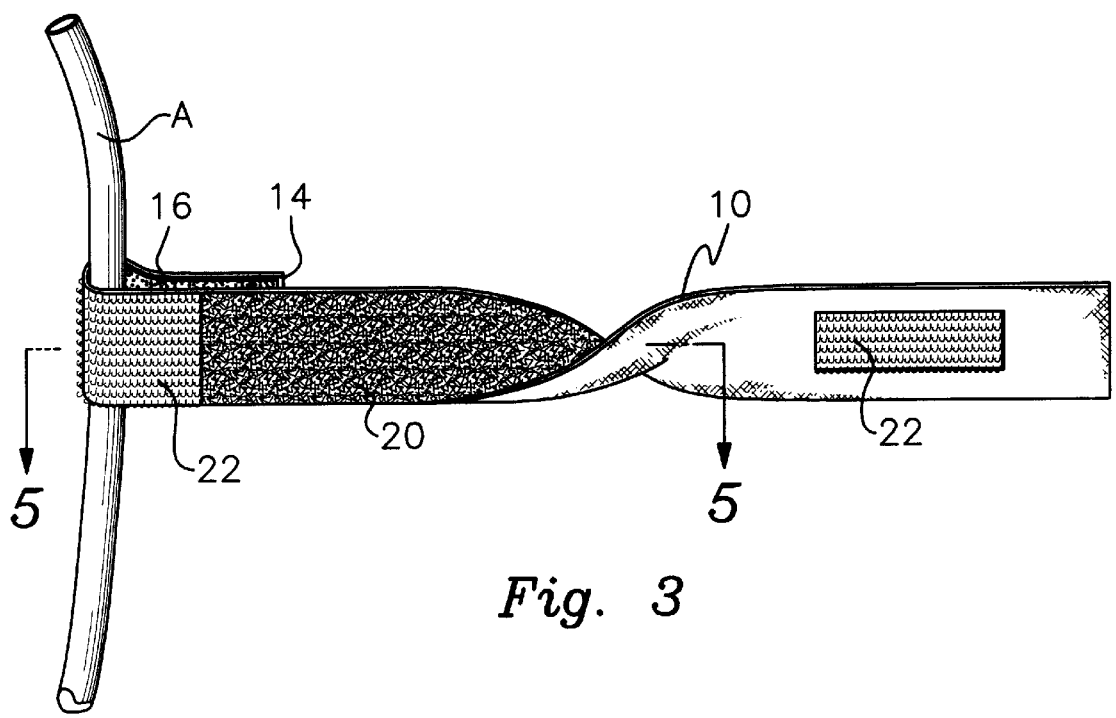
FIG. 3 is another perspective view of the device of FIG. 1 partially wrapped around a catheter tube and twisted at an intermediate point along the body of the device, the tube being partially broken away.
Figure 4A:
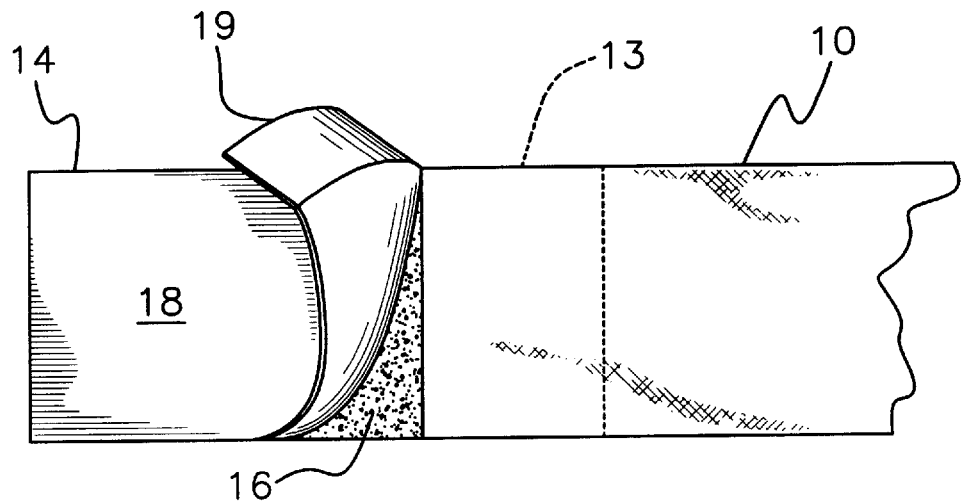
FIG. 4A is a top plan view of the device of FIG. 1, broken away and partially in phantom view.
Figure 4B:
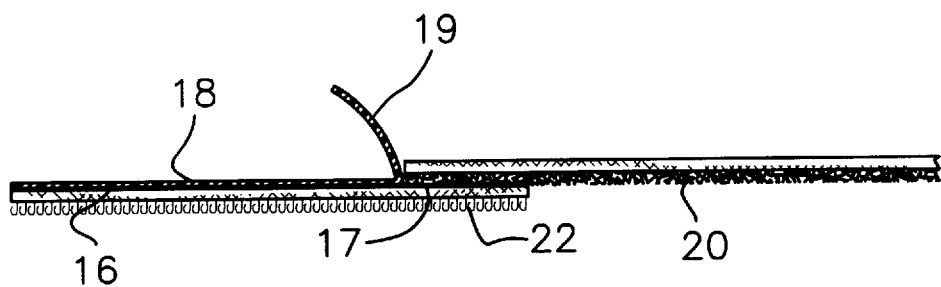
FIG. 4B is a side view of the portion of the device of FIG. 1 illustrated in FIG. 4A.
Figure 5:
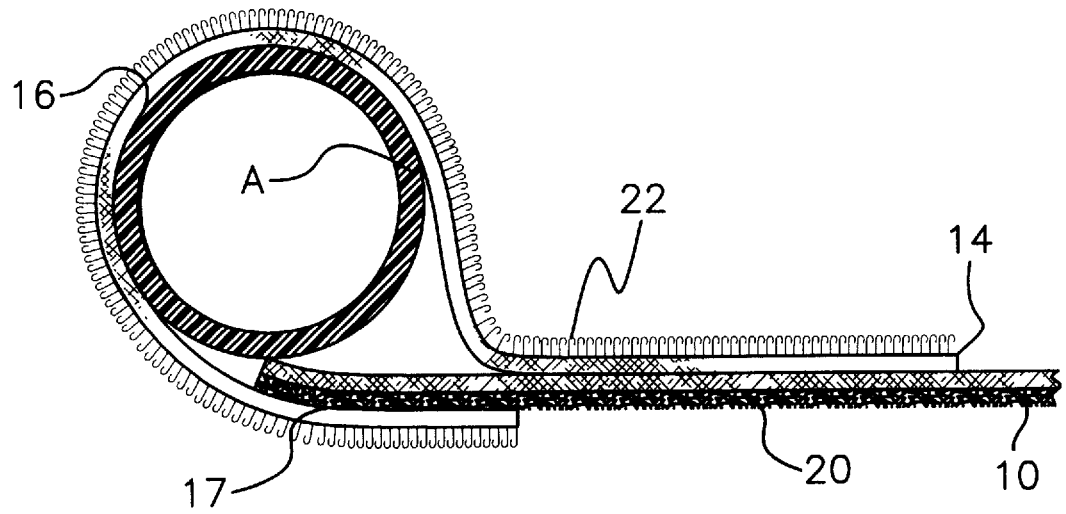
FIG. 5 is a cross-sectional view of the device of FIG. 1, broken away, viewed along line 5—5 shown in FIG. 3.

As will now be appreciated, the novel devices of this invention are simple to use, rugged in construction and conveniently disposable. Moreover, the devices may be quickly positioned and quickly removed, a characteristic which can prove invaluable in the medical field, and especially in the field of emergency medical care. Because of the simplicity of construction, these devices also may be inexpensively produced.

Referring now to the accompanying Figures, FIGS. 1–7 illustrate a preferred embodiment of this invention. The device comprises a primary strap 10 secured to a secondary strap 12 to provide a continuous strap member having inner and outer faces. In this regard, it will be understood that the inner face, during normal use, faces the body part or other object to which the device is attached, while the outer face faces away from the relevant body part or object. Secondary strap 12 is comprised of a connecting end portion 13, a free end portion 14, an adhesive backing which extends over at least a portion of one side (the outer face) of secondary strap 12. When one portion 16 of the adhesive backing residing on free end portion 14 is placed in contact with a generally cylindrical member in the form of a catheter tube A, adhesive backing portion 16 holds tube A in place relative to secondary strap 12. Prior to placing it in contact with tube A, adhesive backing 16 is covered by a removable protective film 18 to facilitate handling of the device and to prolong the useful life of adhesive backing 16. As may be seen from FIGS. 1 and 4A–4B, film 18 extends beyond the point of connection between straps 10 and 12 to form a pull tab 19 which facilitates the rapid removal of film 18 from the adhesive backing portion 16.

The device also has connecting means for connecting strap 12 to strap 10 in the form of another portion 17 of adhesive backing 16. Adhesive portion 17 extends over connecting end portion 13 and is in adhesive contact with Velcro-type female loops 20 (further described below) extending from strap 10. The connecting means of this invention for connecting strap 12 to strap 10 may be one or more of a wide variety of devices capable of securely connecting two pieces of textile material. In addition to the adhesive backing illustrated, non-limiting examples of suitable connecting means include thread, snaps, buttons, and the like.

Figure 6:
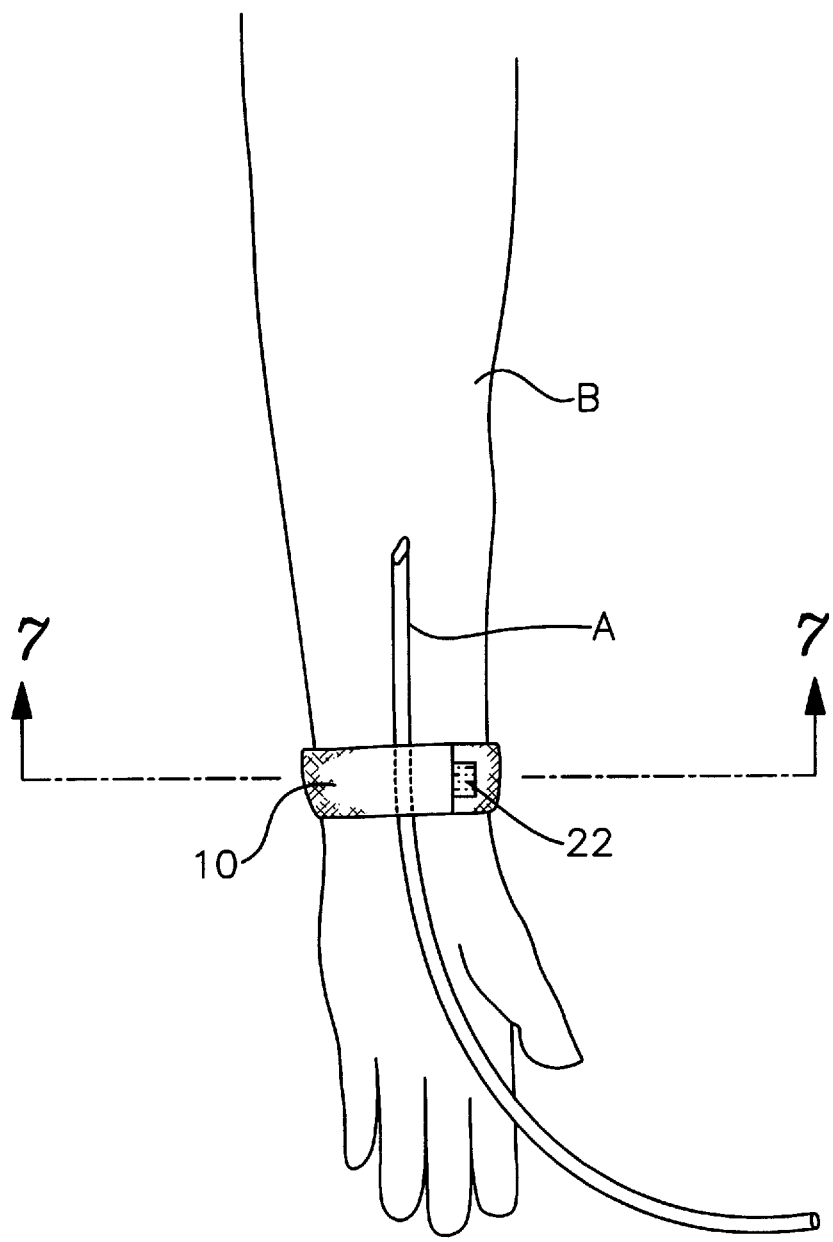
FIG. 6 is a perspective view of the device of FIG. 1 fastened to a patient's arm, the catheter tube being broken away.
Figure 7:
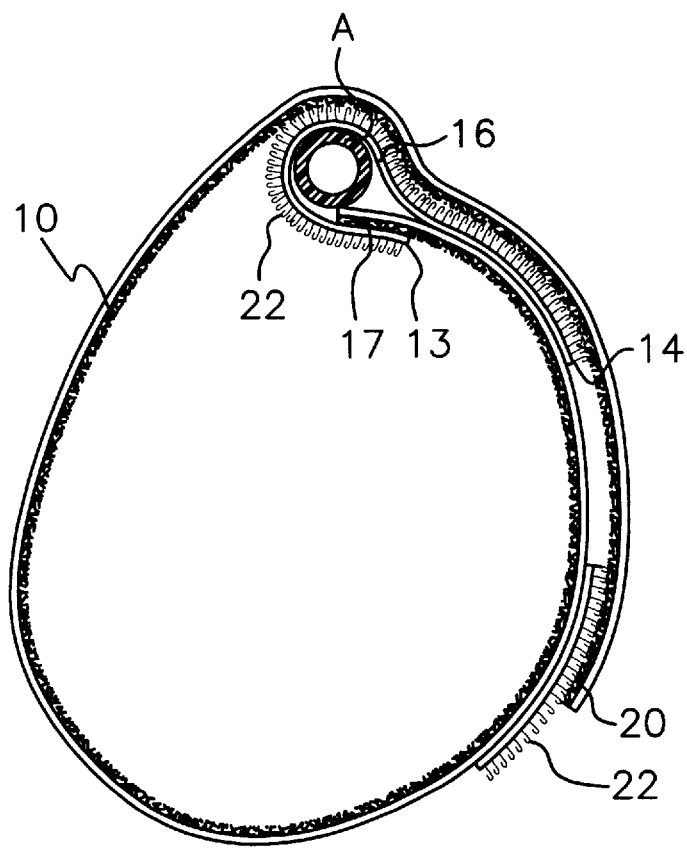
FIG. 7 is a cross-sectional view of the device of FIG. 1 viewed along line 7—7 shown in FIG. 6.

Fastening means in the form of a plurality of Velcro-type female loops 20 extending from one side (inner face) of the primary strap 10, and a plurality of Velcro-type male hooks 22, 22 extending from the other side (outer face) of primary strap 10 and from the non-adhesive side (inner face) of secondary strap 12 are provided for adjustably fastening primary strap 10 around a body part B (depicted as an arm in FIG. 6). As used throughout this specification and the appended claims, "Velcro-type" means of the type employed in separable fasteners such as those described in U.S. Pat. Nos. 2,717,437 and 3,009,235 which are marketed under the registered trademark VELCRO® brand hook and loop fasteners, and VELCRO STICKY BACK® brand strips of hook or loop fasteners with adhesive backing, by Velcro USA, Inc. 406 Brown Avenue, Manchester, N.H. In the device depicted, the Velcro-type male hooks 22 extending from the other side (outer face) of primary strap 10 are part of a single, 0.75 inch wide, 3.75 inches long VELCRO STICKY BACK® brand strip of hook fasteners, the adhesive backing of the strip being in contact with the outer face of strap 10. Of course, the dimensions of this strip and its placement along the length of the primary strap may vary widely, depending upon the size of the relevant body part or other object to which the tube is being secured. The fastening means of this invention may be one or more of a wide variety of devices capable of adjustably fastening the primary strap around the body part or other object to keep the tube or other generally cylindrical member in place during use relative to the body part or other object. In addition to the Velcro-type loop and hook material illustrated, non-limiting examples of suitable fastening means include snaps, buttons, buckles, hooks, and the like.

A variety of dimensions for the primary and secondary straps may be used and are within the scope of this invention. Preferably, the free end of the secondary strap is of sufficient length to be wrapped around at least a major portion (i.e., 180° or more) of the circumference of the generally cylindrical member, e.g., a catheter tube, thereby placing a portion of the adhesive backing in contact with the member. It is also preferred that the free end of the primary strap be of sufficient length to wrap around the relevant body part or other object, and that the primary strap be of sufficient length to place a portion of the plurality of Velcro-type female loops on the primary strap in mating contact with a portion of the plurality of Velcro-type male hooks on the secondary strap. Even more preferably, the free end of the primary strap is of sufficient length to also place a portion of the plurality of Velcro-type female loops in mating contact with a portion of the plurality of male hooks extending from the other side of the primary strap. In the particular embodiment depicted in the figures, the primary strap is 1 inch wide and 17 inches in length, while the secondary strap is 1 inch wide and 3.75 inches in length. Of course, many other dimensions may be used and are within the scope of this invention.

Primary strap 10 and secondary strap 12 of the preferred device depicted in the Figures are in longitudinal alignment when connected to each other. Of course, those skilled in the art will appreciate that the straps alternatively could be connected to each other so that their longitudinal axes are at different angles from one another or are perpendicular, if desired, so long as the contact between the adhesive backing of the secondary strap and the primary strap is sufficient to provide a substantially fixed connection between the straps.

As may be seen from FIGS. 2–3 and 6–7, the device of this invention may be used to detachably secure catheter tube A to body part B by wrapping one end of secondary strap 12 around tube A so that portion 16 of the adhesive backing is in adhering contact with tube A along at least a major portion (i.e., 180° or more) of the circumference thereof, wrapping primary strap 10 around. body part B, placing a portion of the plurality of Velcro-type female loops 20 of primary strap 10 in mating contact with a portion of the plurality of Velcro-type male hooks 22 of secondary strap 12, and preferably, placing another portion of the plurality of Velcro-type female loops 20 in mating contact with a portion of the Velcro-type male hooks 22 extending from the other side of primary strap 10. In this way, the softer surface of the primary strap comprising the female loops is proximate to the surface of the body part, while the primary strap may be wrapped around the body part to place the male hooks and female loops in mating contact, thereby holding the primary and secondary straps in place. Movement of the tube relative to the secondary strap is prevented by the adhesive bond created when the secondary strap is wrapped around the tube along the adhesive backing.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law. In the claims, means-plus-function clauses are intended to cover the structures described herein as performing the cited function and not only structural equivalents but also equivalent structures.

what is claimed is:

1. A device for detachably securing a generally cylindrical member to a body part or other object, the device comprising:
   (a) a primary strap,
   (b) a secondary strap comprising a connecting end portion and a free end portion,
   (c) fastening means for adjustably fastening the primary strap around the body part or other object, and
   (d) connecting means for connecting the connecting end portion to the primary strap, the secondary strap further comprising an adhesive backing which (1) extends over at least a portion of one side of the secondary strap, and (2) when a portion thereof is placed in contact with the member, holds the member in place relative to the secondary strap.

2. A device according to claim 1 wherein the connecting means comprises another portion of the adhesive backing.

3. A device according to claim 2 wherein the fastening means comprises a plurality of female loops extending from one side of the primary strap, and a plurality of male hooks extending from the other side of the primary strap or from the other side of the secondary strap or from both of them.

4. A device according to claim 3 wherein the primary and secondary straps are in longitudinal alignment when connected to one another.

5. A device according to claim 4 further comprising a removable protective film covering the adhesive backing.

6. A device according to claim 1 wherein the fastening means comprises a plurality of female loops extending from one side of the primary strap, and a plurality of male hooks extending from the other side of the primary strap or from the other side of the secondary strap or from both of them.

7. A device according to claim 1 wherein the primary and secondary straps are in longitudinal alignment when connected to one another.

8. A device according to claim 1 further comprising a removable protective film covering the adhesive backing.

9. A device for detachably securing a generally cylindrical member to a body part or other object, the device comprising:
   (a) a primary strap which comprises a plurality of female loops extending from at least a portion of one side of the primary strap,
   (b) a secondary strap which comprises a plurality of male hooks extending from at least a portion of one side of the secondary strap, and an adhesive backing extending over at least a portion of the other side of the secondary strap, one end portion of the secondary strap being connected to one end portion of the primary strap by contact between a first portion of the adhesive backing and a portion of the plurality of female loops, the free end of the secondary strap being of sufficient length to be wrapped around at least a major portion of the circumference of the member thereby placing a second portion of the adhesive backing in contact with the member, and the free end of the primary strap being of sufficient length (1) to be wrapped around the body part or other object, and (2) to place a portion of the plurality of female loops in mating contact with a portion of the plurality of male hooks extending from the secondary strap.

10. A device according to claim 9 wherein the primary and secondary straps are in longitudinal alignment when connected to one another.

11. A device according to claim 9 further comprising a removable protective film covering the adhesive backing.

12. A device according to claim 9 wherein the primary strap further comprises a plurality of male hooks extending from at least a portion of the other side of the primary strap, and wherein the free end of the primary strap is of sufficient length to also place a portion of the plurality of female loops extending from the primary strap in mating contact with a portion of the plurality of male hooks extending from the primary strap.

13. A device according to claim 12 wherein the primary and secondary straps are in longitudinal alignment when connected to one another.

14. A device according to claim 13 further comprising a removable protective film covering the adhesive backing.

15. A method of detachably securing a generally cylindrical member to a body part or other object, the method comprising:
   (a) wrapping around the member one end of a secondary strap, the secondary strap being comprised of a plurality of male hooks extending from at least a portion of one side and an adhesive backing covering at least a portion of the other side, so that a first portion of the adhesive backing is in adhering contact with the member along at least a major portion of the circumference thereof, and
   (b) wrapping around the body part or other objects primary strap, the primary strap being comprised of a plurality of female loops extending from at least a portion of one side, a first portion of the plurality of female loops being in adhering contact with another portion of the adhesive backing of the secondary strap, and
   (c) placing a second portion of the plurality of female loops of the primary strap in mating contact with a portion of the plurality of male hooks of the secondary strap.

16. A method according to claim 15 wherein the primary strap further comprises a plurality of male hooks extending from at least a portion of the other side of the primary strap, and wherein the method further comprises the step of placing a third portion of the plurality of female loops of the one side of the primary strap in mating contact with a portion of the male hooks extending from the other side of primary strap.

17. A device for detachably securing a catheter tube to a body part or other object, the device comprising:
   (a) a primary strap,
   (b) a secondary strap comprising a connecting end portion and a free end portion,
   (c) fastening means for adjustably fastening the primary strap around the body part or other object, the fastening means comprising a plurality of female loops extending from one side of the primary strap, and a plurality of male hooks extending from the other side of the primary strap or from the other side of the secondary strap or from both of them, and
   (d) connecting means for connecting the connecting end portion to the primary strap, the secondary strap further comprising an adhesive backing and a removable protective film covering the adhesive backing, wherein the adhesive backing (1) extends over at least a portion of one side of the secondary strap, and (2) when a portion thereof is placed in contact with the tube, holds the tube in place relative to the secondary strap, wherein the connecting means comprises another portion of the adhesive backing, and wherein the primary and secondary straps are in longitudinal alignment when connected to one another.

18. A device for detachably securing a catheter tube to a body part or other object, the device comprising:

(a) a primary strap, (b) a secondary strap comprising a connecting end portion and a free end portion, (c) fastening means for adjustably fastening the primary strap around the body part or other object, and (d) connecting means for connecting the connecting end portion to the primary strap, the secondary strap further comprising an adhesive backing which (1) extends over at least a portion of one side of the secondary strap, and (2) when a portion thereof is placed in contact with the member, holds the member in place relative to the secondary strap.

19. A device for detachably securing a catheter tube to a body part or other object, the device comprising:

(a) a primary strap which comprises a plurality of female loops extending from at least a portion of one side of the primary strap, (b) a secondary strap which comprises a plurality of male hooks extending from at least a portion of one side of the secondary strap, and an adhesive backing extending over at least a portion of the other side of the secondary strap, one end portion of the secondary strap being connected to one end portion of the primary strap by contact between a first portion of the adhesive backing and a portion of the plurality of female loops, the free end of the secondary strap being of sufficient length to be wrapped around at least a major portion of the circumference of the member thereby placing a second portion of the adhesive backing in contact with the member, and the free end of the primary strap being of sufficient length (1) to be wrapped around the body part or other object, and (2) to place a portion of the plurality of female loops in mating contact with a portion of the plurality of male hooks extending from the secondary strap.

20. A device for detachably securing a catheter tube to a body part or other object, the device comprising:

(a) a primary strap which comprises a plurality of female loops extending from at least a portion of one side of the primary strap, (b) a secondary strap which comprises a plurality of male hooks extending from at least a portion of one side of the secondary strap, and an adhesive backing extending over at least a portion of the other side of the secondary strap, one end portion of the secondary strap being connected to one end portion of the primary strap by contact between a first portion of the adhesive backing and a portion of the plurality of female loops, the free end of the secondary strap being of sufficient length to be wrapped around at least a major portion of the circumference of the tube thereby placing a second portion of the adhesive backing in contact with the tube, and the free end of the primary strap being of sufficient length (1) to be wrapped around the body part or other object, and (2) to place a portion of the plurality of female loops in mating contact with a portion of the plurality of male hooks extending from the secondary strap.

21. Apparatus which comprises a catheter tube and a device for detachably securing the catheter tube to a body part or other object, the device comprising:

(a) a primary strap, (b) a secondary strap comprising a connecting end portion and a free end portion, (c) fastening means for adjustably fastening the primary strap around the body part or other object, and (d) connecting means for connecting the connecting end portion to the primary strap, the secondary strap further comprising an adhesive backing which (1) extends over at least a portion of one side of the secondary strap, and (2) when a portion thereof is placed in contact with the tube, holds the tube in place relative to the secondary strap.

* * * * *

UNITED STATES PATENT AND TRADEMARK OFFICE
CERTIFICATE OF CORRECTION

PATENT NO. : 5,879,335
DATED : March 9, 1999
INVENTOR(S) : Martinez et al.

It is certified that error appears in the above-identified patent and that said Letters Patent is hereby corrected as shown below:

On the title page, under References Cited, U.S. Patent Documents, insert --5,205,832 4/1993 Tuman 604/179--.

Claim 15, column 6, line 34, reads "objects" and should read --object a--.

Signed and Sealed this

Thirteenth Day of July, 1999

Q. TODD DICKINSON

Attest:

*Attesting Officer*    *Acting Commissioner of Patents and Trademarks*